United States Patent [19]

Korsatko-Wabnegg et al.

[11] Patent Number: 5,183,666
[45] Date of Patent: Feb. 2, 1993

[54] PRESSING NOT DELAYED RELEASE OF ACTIVE COMPOUND, PROCESS FOR ITS PRODUCTION AND USE OF POLYHYDROXYBUTYRIC ACID FOR THE PRODUCTION OF SUCH A PRESSING

[75] Inventors: Brigitta Korsatko-Wabnegg; Werner Korsatko, both of Graz, Austria

[73] Assignee: PCD Polymere Gesellschaft m.b.H., Schwechat-Mannsworth, Austria

[21] Appl. No.: 606,162

[22] Filed: Oct. 31, 1990

[30] Foreign Application Priority Data

Nov. 30, 1989 [AT] Austria ................. 2734/89

[51] Int. Cl.$^5$ ............................... A61K 9/14
[52] U.S. Cl. .................... 424/464; 424/465; 424/468; 424/501
[58] Field of Search ............... 424/464, 465, 468, 472, 424/474, 479, 480, 482, 99

[56] References Cited

U.S. PATENT DOCUMENTS

| 4,491,575 | 1/1985 | Korsatko ........................ 424/19 |
| 4,576,740 | 3/1986 | Hall et al. ..................... 252/522 R |
| 4,786,598 | 11/1988 | Lafferty et al. .................. 435/146 |

FOREIGN PATENT DOCUMENTS

| 0025696 | 3/1981 | European Pat. Off. . |
| 0052459 | 12/1985 | European Pat. Off. . |
| 172422 | 2/1986 | European Pat. Off. . |
| 3417576 | 11/1985 | Fed. Rep. of Germany . |
| 3712095 | 10/1988 | Fed. Rep. of Germany . |
| WO89/04673 | 6/1989 | PCT Int'l Appl. . |

OTHER PUBLICATIONS

Remingtons Pharmaceutical Sciences, Mack Publishing Co., 1990.
Austrian Codex 1986/87, Osterreichischer Apotheker Verlag, Wien 1986, Seite 473, Gutron Tablets.
H. V. Czetscu-Lindenwald, et al., "Hilfsstoffe fur Pharmazie und angrezende Gebiete," 2. Auflage, Editio Cantor K. G., Aulendorf, 1963, Siete 314.
R. Mank, Darstellung Peroraler Retardarzneiformen auf der Basis von abbaubaren Polymeren, "Pharmazie" 44 (H.B.) 545-547 (1989).

Primary Examiner—Thurman K. Page
Assistant Examiner—N. Levy
Attorney, Agent, or Firm—Wenderoth, Lind & Ponack

[57] ABSTRACT

Pressing containing homo- and/or copolymers of D(−)-3-hydroxybutyric acid, at least one solid disintegrant and at least one solid pharmaceutical active compound, process for its production and the use of homo- and/or copolymers of D(−)-3-hydroxybutyric acid for the production of such a pressing.

6 Claims, No Drawings

PRESSING NOT DELAYED RELEASE OF ACTIVE COMPOUND, PROCESS FOR ITS PRODUCTION AND USE OF POLYHYDROXYBUTYRIC ACID FOR THE PRODUCTION OF SUCH A PRESSING

The invention relates to a pressing for oral administration which has no active compound release-delaying properties, consisting of a homo- and/or copolymer of D(−)-3-hydroxybutyric acid (poly-HB), at least one disintegrant, at least one pharmaceutical active compound and, if appropriate, auxiliaries customary in pharmaceutical technology, process for its production and the use of poly-HB for the production of such a pressing.

In U.S. Pat. No. 4,491,575 is described that poly-D(−)-3-hydroxybutyric acid has slight elastic properties, a slight tendency for electrostatic charge and good lubricating and glidant properties, and that pressings having good active compound release-delaying properties can be produced from poly-D(−)-3-hydroxybutyric acid and a pharmaceutical active compound.

Such delayed-release forms are used if the pharmaceutically active compound is intended to be delivered in a sustained manner over a relatively long period. In very many cases, however, it is necessary that the release of the active compound is not delayed, but immediate. Customarily, for the production of such non-release-delaying pressings the pharmaceutically active compound is mixed with auxiliaries before compressing, in which case, however, the suitability of these auxiliaries, for example with respect to their compression properties is not always completely satisfactory.

It has now unexpectedly been found that poly-HB, in spite of its release-delaying properties, can be used for the production of compressed medicament forms from which on administration the active compound is immediately released and its release is not delayed if a mixture of pharmaceutical active compound, poly-HB and a disintegrant are mutually compressed. Surprisingly, however, a stable matrix is formed in which the pharmaceutically active compound is embedded, the addition of the disintegrant not impairing the good processing properties of the mixture. Such compressed medicaments thus represent an enrichment of the technology.

The invention therefore relates to a pressing for oral administration having non-delayed release of active compound, comprising a homo- and/or copolymer of D(−)-3-hydroxybutyric acid, at least one solid disintegrant and at least one solid pharmaceutically active compound.

Homo- and/or copolymers of D(−)-3-hydroxybutyric acid (poly-HB) to be are understood as meaning both homo-and copolymers of D(−)-3-hydroxybutyric acid and mixtures thereof, homopolymers being preferred. Homopolymers of D(−)-3-hydroxybutyric acid can be prepared, for example, by the procedure described in U.S. Pat. No. 4,786,598 and copolymers by the procedure described in EP-A-0,052,459. The poly-HB customarily used has a molecular weight of about 25,000 to 1,000,000, preferably from about 50,000 to 800,000. Poly-HB is present to a proportion of about 10 to 90 per cent by weight in powder form or pregranulated in the pressing according to the invention.

Disintegrants are to be understood as meaning additives which abolish the release-delaying properties of poly-HB, but not its good compression properties. Examples of such disintegrants, are disclosed, for example, in the Lehrbuch der pharmazeutischen Technologie (Textbook of Pharmaceutical Technology), R. Voigt, 5th edition, Verlag Chemie, Weinheim (1984), pages 182 et seq. Disintegrants are preferably present in the pressing according to the invention which increase the capillarity of the pressing, absorb moisture and swell, such as, for example, microcrystalline cellulose, crosslinked sodium carboxymethylcellulose, crosslinked polyvinylpyrrolidone, sodium carboxymethyl starch, and the calcium salt of the polycarboxymethyl ether of cellulose and similar compounds.

The amount of the disintegrant in the pressing according to the invention is dependent on the amount of poly-HB used, and on the disintegrating power of the disintegrants used. The required amount can be determined for any disintegrant by simple tests and is in general between 0.5 to 70% by weight in the pressing.

Solid pharmaceutical active compounds are to be understood as meaning solid pharmaceutical active compounds or mixtures thereof, it being possible for the active compounds to be present in the pressing in free form, in the form of pharmacologically tolerable salts, in powder form or granulated. The proportion of the active compound in the pressing according to the invention depends on the nature of the active compound and its area of application. In general, the pressing contains 5 to 80% by weight of active compound.

The pressing may consist exclusively of poly-HB, active compound and distintegrant, but it is also possible that it moreover contains customary pharmaceutical auxiliaries, such as, for example, fillers, binders, glidants and lubricants, colourants and so on, which can be present in powder form or pregranulated. It has been established that it is possible to replace a part of the poly-HB by lactose, which is less expensive than poly-HB. Replacing a part of the poly-HB by lactose is a preferred embodiment of the invention. A minimum proportion of about 10% by weight of poly-HB must be present in the pressing, however, for the formation of a stable matrix. Examples of auxiliaries which can be present in the pressing according to the invention are described in the Lehrbuch der pharmazeutischen Technologie (Textbook of Pharmaceutical Technology), R. Voigt, 5th edition, Verlag Chemie, Weinheim, (1984), page 178 et seq., in particular under items 8.5.2., 8.5.3. and 8.5.4.

The disintegrant properties of the pressing depend on the nature and amount of the components of the pressing used, on their particle size and on the press pressure used. In general the pressing disintegrates more rapidly the higher the proportion of the disintegrant in the pressing and the lower the press pressure, where the press pressure should customarily not be less than 0.5 tons/tablet, as otherwise the breaking strength of the pressing is too low. The high disintegration rate desired can thus be determined by simple tests by variation of the various parameters.

The invention further relates to a process for the production of a pressing having non-delayed release of active compound, which is characterized in that a homo- and/or copolymer of D(−)-3-hydroxybutyric acid is mixed thoroughly with at least one solid disintegrant and at least one solid pharmaceutical active compound with or without auxiliaries customary in pharmaceutical technology and the mixture is compressed with or without pregranulation.

In the case of small amounts, the mixing can be carried out by means of mortar and pestle or a powder mixing container. Large batches can be thoroughly mixed with the aid of rotating drums, paddle mixers, plate mixers, mixing screws, ribbon mixers, cone mixers, double cone mixers and V-mixers (twin shell blenders) and so on. The mixtures obtained are compressed to give tablets or coated tablet cores of any desired form and size. It is also possible to produce small compressed articles for filling into capsules or for the production of multilayer tablets. Preferably, the mixtures are compressed directly and without further treatment. However, they can also be pregranulated in a customary manner before compressing. The production of the pressings is possible using all conventional tablet presses, such as, for example, eccentric presses, rotary presses and hydraulic presses and so on, it being possible to vary the press pressure, for example, over a range of 0.5 to 10 tons, i.e. 49.05–981N per tablet.

Owing to the matrix-forming properties of the poly-HB, the pressing according to the invention can be produced by simple compression of the powder mixtures and has an excellent storage stability. It is not necessary to pregranulate the powder mixture before compression. Simple compression of the powder mixtures is therefore a preferred embodiment of the invention. A most preferred embodiment of the invention comprises mixing powders of solid poly-D(−)-3-hydroxybutyric acid, of solid sodium carboxymethyl cellulose, of a solid active ingredient with or without a powder of lactose and compressing to get a pressing containing at least 10% by weight of poly-D(−)-3-hydroxybutyric acid, 0,5 to 70% by weight of sodium carboxymethyl cellulose, 5 to 80% by weight of an active ingredient with or without lactose.

A poly-HB of molecular weight 97,000 and a particle size fraction of 125 to 200 micrometers was used in the examples. 2-Amino-N-(2-(2,5-dimethoxyphenyl)-2-hydroxyethyl)acetamide HCl (midodrine HCl) was chosen as the active compound.

The respective components were homogeneously mixed, and compressed to give tablets by means of an electrohydraulic press without pregranulation. The average weight of the tablets, if not stated otherwise, was 100±3 mg, the diameter of the tablets was 7 mm and the height was about 2 mm.

The release rate of the active compound was in some cases determined by the half-change method, in which the pH is continuously increased from pH 1.3 to pH 7.3 in the course of 8 hours, the amount of active compound released being investigated at intervals of 30 minutes. The quantitative detection of midodrine is carried out by spectrophotometry at 289 nm. The measurement of the disintegration times was carried out at various pH values by the method disclosed in the Europäischen Arzneibuch (European Pharmacopoeia), volume III, (1981) page 78 et seq. In this case, the respective residues were dried and gravimetrically determined after the respective time. In the case of tablets which contained midodrine HCl, quantitative detection of the amounts of active compound released was determined by spectrophotometry at 289 nm (disintegration test).

pH 1 buffer: Titrisol buffer Merck Art. No. 9881
pH 4 buffer: Titrisol buffer Merck Art. No. 9884
pH 7 buffer: Titrisol buffer Merck Art. No. 9887
pH 7.4 buffer: Sörensen phosphate buffer
$Na_2HPO_4.12H_2O$ ... 41.246 g
$KH_2PO_4$ ... 2.8 g
double-distilled water ... to 1000.0 ml

EXAMPLE 1

Production of placebo tablets from poly-HB and Primojel (sodium carboxymethyl starch, W. A. Scholten's Chem. Fabriken N.V., Foxhol, NL)

Tablets of various composition were produced from poly-HB and Primojel at a press pressure of 2 tons per tablet. The tablets had a weight of 150 mg, a diameter of 8 mm and a height of 2.5±1 mm. The settled apparent density increased from 0.30 g/ml (10% by weight of Primojel) to 0.39 g/ml (50% by weight of Primojel), the compacted apparent density from 0.37 g/ml (10% by weight of Primojel) to 0.56 g/ml (50% by weight of Primojel), and the breaking strength was more than 20 kp, in the case of 50% Primojel content exactly 20 kp. The disintegration times were determined at various pH values with the aid of the disintegration test. The results are summarized in Table 1:

TABLE 1

| Primojel % by weight | pH 1 | pH 4 | pH 7.4 |
|---|---|---|---|
| | | Disintegration time in minutes | |
| 10 | 241 | 260 | 260 |
| 20 | 62 | 70 | 67 |
| 30 | 30 | 30 | 29 |
| 40 | 18 | 20 | 17 |
| 50 | 10 | 11 | 13 |

EXAMPLE 2

Production of tablets consisting of poly-HB, Primojel and 2-amino-N-(2-(2,5-dimethoxyphenyl)-2-hydroxyethyl)acetamide HCl (midodrine HCl)

Tablets of weight about 150 mg, of diameter 8 mm, of height 2.5 mm, of settled apparent density 0.27 g/ml, of compacted apparent density 0.40 g/ml and of breaking strength more than 20 kp, which contained 2.25% by weight of Primojel, were produced at a press pressure of 2 tons per tablet from 131.63 parts by weight (p.b.w.) of poly-HB, 3.37 p.b.w. of Primojel and 15 p.b.w. of midodrine HCl. The release of the active compound was checked by the half-change method. Accordingly, after 30 minutes about 20%, after 1½ hours about 35% and after 4 hours virtually 100% of the active compound was released.

EXAMPLE 3

Production of tablets consisting of poly-HB, Primojel and midodrine HCl

Tablets having a breaking strength of 16.2 kp, which contained 6.4% by weight of Primojel, were produced at a press pressure of 2 tons per tablet from 78.56 p.b.w. of poly-HB, 6.44 p.b.w. of Primojel and 15 p.b.w. of midodrine HCl. The release of the active compound was checked by the half-change method. Accordingly, after 30 minutes over 40%, after 1½ hours almost 90% and after 2 hours virtually 100% of the active compound was released.

EXAMPLE 4

Production of tablets consisting of poly-HB, Primojel and midodrine HCl

Tablets of weight 150 mg, of diameter 8 mm and of compacted apparent density 0.40 g/ml, which contained 4.5% by weight of Primojel, were produced at various press pressures from 128.25 p.b.w. of poly-HB, 15 p.b.w. of midodrine HCl and 6,75 p.b.w. of Primojel. The breaking strength was virtually independent of the press pressures used and was between 16 and 20 kp. The disintegration times were determined at pH 1 with the aid of the disintegration test and are shown in Table 2.

TABLE 2

| Press pressure (tons/tablet) | | | | | |
|---|---|---|---|---|---|
| 0.5 | 1 | 2 | 3 | 4 | 5 |
| Active compound released (% by weight): | | | | | |
| after 30 minutes | | | | | |
| 86.8 | 46.2 | 38.5 | 35.8 | 29.1 | 28.1 |
| after 90 minutes | | | | | |
| 95.5 | 88 | 84 | 88 | 76.5 | 65.8 |
| after 120 minutes | | | | | |
| 97 | 95 | 95 | 95 | 88.5 | 79.2 |

EXAMPLE 5

Production of tablets consisting of poly-HB, Polyplasdone XL (crosslinked polyvinylpyrrolidone, General Aniline and Film Corporation, N.Y.) and midodrine HCl 83.64. p.b.w. of poly-HB, 1.36 p.b.w. of polyplasdone XL and 15 p.b.w. of midodrine HCl were compressed to give tablets, which have a breaking strength of 18 kp, at a press pressure of 2 tons per tablet. The release of the active compound was checked by the half-change method. After half an hour 46%, after 1½ hours 90% and after 2 hours almost 100% of the active compound was released.

EXAMPLE 6

Production of tablets consisting of poly-HB, Ac-Di-Sol (sodium carboxymethylcellulose, Lehmann and Voss, Hamburg, FRG) and midodrine HCl 83.64 p.b.w. of poly-HB, 1.36 p.b.w. of Ac-Di-Sol and 15. p.b.w. of midodrine HCl were compressed to give tablets, which had a breaking strength of 18.3 kp and contained 1.36% by weight of Ac-Di-Sol, at a press pressure of 2 tons per tablet. The release of the active compound was checked by the half-change method. After half an hour 45.6%, after 1½ hours more than 90% and after 2 hours virtually 100% of the active compound was released.

EXAMPLE 7

Production of placebo tablets consisting of poly-HB and Ac-Di-Sol

Tablets of settled apparent density increasing from 0.26 g/ml (10% by weight of Ac-Di-Sol) to 0.37 g/ml (50% by weight of Ac-Di-Sol), of compacted apparent density increasing from 0.40 g/ml (10% by weight of Ac-Di-Sol) to 0.43 g/ml (50% by weight of Ac-Di-Sol) and of breaking strength of more than 20 kp were produced from differing parts by weight of poly-HB and Ac-Di-Sol. The disintegration times were determined at differing pH values by means of the disintegration test; they are summarized in Table 3.

TABLE 3

| Ac-Di-Sol (% by weight) | pH | Decomposition time (minutes) |
|---|---|---|
| 10 | 1 | 90 |
|  | 4 | 63 |
|  | 7 | 59 |
| 20 | 1 | 16 |
|  | 4 | 12 |
|  | 7 | 11 |
| 30 | 1 | 10 |
|  | 4 | 8 |
|  | 7 | 7 |
| 40 | 1 | 7 |
|  | 4 | 6 |
|  | 7 | 6 |
| 40 | 1 | 3.5 |
|  | 4 | 3 |
|  | 7 | 3 |

EXAMPLE 8

Production of placebo tablets from poly-HB and E.C.G. 505 (calcium salt of the polycarboxymethyl ether of cellulose, Lehman and Voss, Hamburg, FRG)

Tablets of weight 150 mg and of diameter 8 mm which had a settled apparent density increasing from 0.28 g/ml (10% by weight of E.C.G. 505) to 0.33 g/ml (50% by weight of E.C.G. 505), a compacted apparent density increasing from 0.34 g/ml (10% by weight of E.C.G. 505) to 0.49 g/ml (50% by weight of E.C.G. 505) and breaking strenght which in all cases was higher than 20 kp, were produced at a press pressure of 2 tons per tablet from differing weight proportions of poly-HB and E.C.G. 505. The disintegration times at differing pH values were determined with the aid of the disintegration test and are shown in Table 4.

TABLE 4

| E.C.G. 505 (% by weight) | pH 1 | pH 4 Disintegration time (min) | pH 7.4 |
|---|---|---|---|
| 10 | 260 | 226 | 211 |
| 20 | 139 | 113 | 111 |
| 30 | 45 | 43 | 52 |
| 40 | 35 | 31 | 30 |
| 50 | 30 | 25 | 22 |

EXAMPLE 9

Production of tablets consisting of poly-HB, E.C.G. 505 and midodrine HCl

Tablets of weight 150 mg which had a settled apparent density of 0.24 g/ml, a compacted apparent density of 0.35 g/ml and a breaking strength of more than 20 kp were produced at a press pressure of 2 tons per tablet from 128.25 p.b.w. of poly-HB, 6.75 p.b.w. of E.C.G. 505 and 15 p.b.w. of midodrine HCl. The release rate of the midodrine HCl was determined by the halfchange method. In this case, after half an hour 26%, after 1½ hours 60% and after 3 hours virtually 100% of the active compound was released.

EXAMPLE 10

Production of tablets consisting of poly-HB, E.C.G. 505 and midodrine HCl

Tablets having the properties shown in Example 9 were produced at various press pressures from 128.25 p.b.w. of poly-HB, 6.75 p.b.w. of E.C.G. 505 and 15 p.b.w. of midodrine HCl. The release of the active compound was checked at a pH of 1 by means of the disintegration test. The results are summarized in Table 5.

TABLE 5

| Press pressure (tons/tablet) | | | | | |
|---|---|---|---|---|---|
| 0.5 | 1 | 2 | 3 | 4 | 5 |
| Active compound released (% by weight): | | | | | |
| after 30 minutes | | | | | |
| 80.8 | 41.8 | 33.1 | 34.2 | 28.7 | 26.5 |
| after 90 minutes | | | | | |
| 98.4 | 83.5 | 81.3 | 87.6 | 77.9 | 77.7 |
| after 120 minutes | | | | | |
| 98.9 | 93.4 | 93.6 | 95.8 | 91.4 | 86.3 |

EXAMPLE 11

Production of placebo tablets from poly-HB and Avicel PH (microcrystalline cellulose, Lehmann and Voss, Hamburg, FRG)

7 p.b.w. of poly-HB and 3 p.b.w. of Avicel of particle size 71 to 100 μm were compressed at a press pressure of 2 tons per tablet to give tablets which contained 30% by weight of Avicel. The settled apparent density was 0.27 g/ml, the compacted apparent density 0.33 g/ml and the breaking strength more than 20 kp. The tablets began to disintegrate in the disintegration test after 15 minutes at a pH of 7, and after 9 minutes at a pH of 1.

Tablets consisting of poly-HB and Avicel PH of particle size 71 to 100 μm in the weight ratio 9:1, which had been prepared in the above-described manner and which had a settled apparent density of 0.27 g/ml, a compacted apparent density of 0.34 g/ml and a breaking strength of more than 20 kp, on the other hand neither disintegrated at a pH of 7 nor at a pH of 1 within 24 hours in the in vitro test.

EXAMPLE 12

Production of placebo tablets consisting of poly-HB and Avicel PH

Tablets consisting of poly-HB and Avicel in the weight ratio 6:4 and 5:5 were produced at a press pressure of 2 tons per tablet. Their settled apparent density increased from 0.27 g/ml (40% by weight of Avicel) to 0.31 g/ml (50% by weight of Avicel), the compacted apparent density was 0.43±2 mg and the breaking strength was higher than 20 kp. The disintegration times were determined at various pH values with the aid of the disintegration test and are shown in Table 6.

TABLE 6

| Avicel PH % by weight | pH 1 | pH 4 | pH 7.4 |
|---|---|---|---|
| | Disintegration time (start of disintegration) | | |
| 40 | 113 min | 208 min | 280 min |
| | (9 min) | (14 min) | (11 min) |
| 50 | 100 min | 30 min | 130 min |
| | (8 min) | (9 min) | (9 min) |

EXAMPLE 13

Production of tablets consisting of poly-HB, Ac-Di-Sol, midodrine HCl and lactose 25 p.b.w. of poly-HB, 2.5 p.b.w. of Ac-Di-Sol, 5 p.b.w. of midodrine HCl and 32.5 p.b.w. of lactose were homogeneously mixed and compressed at a press pressure of 0.5 tons/tablet to give tablets of weight 65 mg, of diameter 6 mm, of height 1.8 mm and of breaking strength 6 kp. The disintegration times were determined at a pH of 1 by means of the disintegration test. The tablets disintegrated completely within one minute.

What we claim is:

1. Pressing for oral administration having non-delayed release of active compound comprising at least one solid pharmaceutically active compound and as matrix material a homo- and/or copolymer of D(—)-3-hydroxybutyric acid and an amount of at least one solid disintegrant sufficient to cancel the delayed release properties of the homo- and/or copolymer of D(—)-3-hydroxybutyric acid.

2. Pressing according to claim 1 wherein
the solid disintegrant increases the capillarity of the pressing, absorbing moisture and swelling.

3. Pressing according to claim 1 or 2, wherein
the solid disintegrant is microcrystalline cellulose, crosslinked sodium carboxymethylcellulose, crosslinked polyvinylpyrrolidone, sodium carboxymethyl starch or the calcium salt of the polycarboxymethyl ether of cellulose.

4. pressing according to claim 1, further comprising at least one of fillers, binders, glidants, lubricants or colorants.

5. Pressing according to claim 1, comprising lactose.

6. A process for the production of a pressing having non-delayed release of a pharmaceutically active compound, which comprises thoroughly mixing a homo- and/or copolymer of D(—)-3-hydroxybutyric acid with an amount of at least one solid disintegrant sufficient to cancel the delayed release properties of the homo- and/or copolymer of D(—)-3-hydroxybutyric acid, and at least one solid pharmaceutically active compound to form a mixture and compressing the mixture with or without pregranulation.

* * * * *